(12) United States Patent
Klammt et al.

(10) Patent No.: US 11,921,108 B2
(45) Date of Patent: Mar. 5, 2024

(54) METHODS FOR DETERMINING AMOUNT OF FUNCTIONAL ALBUMIN

(71) Applicant: Fraunhofer-Gesellschaft zur Förderung der angewandten Forschung e.V., Munich (DE)

(72) Inventors: Sebastian Klammt, Berlin (DE); Steffen Mitzner, Rostock (DE); Jan Stange, Rostock (DE); Emil Reisinger, Rostock (DE)

(73) Assignee: FRAUNHOFER-GESELLSCHAFT ZUR FÖRDERUNG DER ANGEWANDTEN FORSCHUNG E.V., Munich (DE)

( * ) Notice: Subject to any disclaimer, the term of this patent is extended or adjusted under 35 U.S.C. 154(b) by 69 days.

(21) Appl. No.: 17/667,376

(22) Filed: Feb. 8, 2022

(65) Prior Publication Data

US 2022/0163517 A1    May 26, 2022

Related U.S. Application Data

(62) Division of application No. 16/607,064, filed as application No. PCT/EP2018/060176 on Apr. 20, 2018, now Pat. No. 11,280,780.

(30) Foreign Application Priority Data

Apr. 21, 2017 (DE) ..................... 10 2017 206 786.1

(51) Int. Cl.
*G01N 33/53* (2006.01)
*G01N 33/543* (2006.01)
*G01N 33/68* (2006.01)

(52) U.S. Cl.
CPC ... *G01N 33/54306* (2013.01); *G01N 33/6803* (2013.01); *G01N 2333/765* (2013.01)

(58) Field of Classification Search
None
See application file for complete search history.

(56) References Cited

U.S. PATENT DOCUMENTS

| | | | |
|---|---|---|---|
| 6,699,722 B2 | 3/2004 | Bauer | |
| 8,080,153 B2 | 12/2011 | Feldman | |
| 2010/0068826 A1 | 6/2010 | Gokhan | |

FOREIGN PATENT DOCUMENTS

| | | |
|---|---|---|
| EP | 1 315 973 B1 | 7/2009 |
| WO | WO 02/23198 A2 | 3/2002 |
| WO | WO 2016/012812 A1 | 1/2016 |

OTHER PUBLICATIONS

Altamentova et al., A Florescence Method For Estimation Of Toxemia: Binding Capacity Of Lipoproteins And Albumin In Plasma, Clinica Chimica Acta, vol. 271, pp. 133-139, 1998.
Blencowe et al., Benzodiazepine Whole Blood Concentrations in Cases With Positive Oral Fluid On-site Screening Test Results Using the Drug wipe Single for Benzodiazepines, Journal of Analytical Toxicology, vol. 35, pp. 349-356, 2011.
Brodersen et al., Determination of Reserve Albumin-Equivalent for Ligand binding Probing Two Distinct Binding Functions of the Protein, Analytical Biochemistry, vol. 121, pp. 395-408, 1982.
Dou et al., The Uremic Solutes P-Cresol And Indoxyl Sulfate Inhibit Endothelial Proliferation And Wound Repair, Kidney International, vol. 65, pp. 442-451, 2004.
Fasano, et al., The Extraordinary Ligand Binding Properties of Human Serum Albumin, Life, vol. 57, No. 12, pp. 787-796, 2005.
Ghuman et al., Structural Basis of the Drug-Binding Specificity of Human Serum Albumin, Journal of Molecular Biology, vol. 353, pp. 38-52, 2005.
Heemann, et al., Albumin Dialysis in Cirrhosis With Superimposed Acute Liver Injury: A Prospective, Controlled Study, Hepatology, vol. 36, pp. 949-958, 2002.
Hinz et al., S118, Abstract 087, Albumin function is reduced in severe sepsis, Infection, 39 (Suppl 2), S93-S151, 2011.
Hughes, R.D., Review Of Methods To Remove Protein-Bound Substances In Liver Failure, The International Journal of Artificial Organs, vol. 25, No. 10, pp. 911-917, 2002.
Klammt et al., Albumin-Binding Function Is Reduced In Patients With Decompensated Cirrhosis And Correlates Inversely With Severity Of Liver Disease Assessed By Model For End-Stage Liver Disease, Eur J Gastroenterol Hepatol, vol. 19, No. 3, pp. 257-263, 2007.
Klammt, et al., Albumin-Binding Capacity (Abic) Is Reduced In Patients With Chronickidney Disease Along With An Accumulation Of Protein-Bound Uraemic Toxins, Nephrol Dial Transplant, vol. 27, pp. 2377-2383, 2012.
Klammt, et al., Improvement of Impaired Albumin Binding Capacity in Acute-on-Chronic Liver Failure by Albumin Dialysis, Liver Transplantation, vol. 14, pp. 1333-1339, 2008.
Kragh-Hansen et al., Practical Aspects of the Ligand-Binding and Enzymatic Properties of Human Serum Albumin, Biological and Pharmaceutical Bulletin, vol. 25, No. 6, pp. 695-704, 2002.
Lee, et al., Review: Modifications of Human Serum Albumin and Their Binding Effect, Current Pharmaceutical Design, vol. 21, No. 14, pp. 1862-1865, 2015.
Liabeuf et al., Protein-Bound Uremic Toxins: New Insight from Clinical Studies, Toxins, vol. 3, pp. 911-919, 2011.

(Continued)

*Primary Examiner* — Gary Counts
(74) *Attorney, Agent, or Firm* — Knobbe, Martens, Olson & Bear LLP

(57) ABSTRACT

A method for determining an amount of functional albumin includes providing a test sample containing a defined amount of albumin of unknown binding capacity and a reference sample containing the same defined amount of albumin having a reference binding capacity, incubating the test and reference samples with a defined amount of at least one albumin-binding marker M under conditions that allow formation of complexes of the at least one albumin-binding marker M and albumin (M:A), removing the complexes, detecting a presence or an amount of unbound marker M in the samples after removal of the complex (M:A) through a first and a second test strips that allow for a determination of an amount of unbound marker M, and determining the amount of functional albumin based on the presence or the amount detected of marker M.

13 Claims, 3 Drawing Sheets

(56) References Cited

OTHER PUBLICATIONS

Munzert, Eberhard, English translation of WO2002/023198, Indirect method for the quantitative analysis of the b inding capacity present in an aqueous protein solution. Machine translation, pp. 1-5, 2002.

Oettl, et al., Oxidative Albumin Damage in Chronic Liver Failure: Relation to Albumin Binding Capacity, Liver Dysfunction and Survival, Journal of Hepatology, vol. 59, pp. 978-983, 2013.

Sen et al., Emerging indications for albumin dialysis, The American Journal of Gastroenterology, vol. 100, pp. 468-475, 2005.

Sudlow, et al., The Characterization of Two Specific Drug Binding Sites on Human Serum Albumin, Molecular Pharmacology, vol. 11, pp. 824-832, 1975.

International Preliminary Report on Patentability, dated Oct. 22, 2019, in International Application No. PCT/EP2018/060176.

International Search Report, dated Jun. 12, 2018, in International Application No. PCT/EP2018/060176.

Written Opinion, dated Jun. 12, 2018 in International Application No. PCT/EP2018/060176.

Friedman, M., Analysis, Nutrition, and Health Benefits of Tryptophan, International Journal of Tryptophan Research, vol. 11, pp. 1-12, 2018.

Wu, Z., et al., Comparison of critical methods developed for fatty acid analysis: A review, Journal of Separation Science, vol. 40, pp. 288-298, 2017.

Diazepam concentration [μmol/l] in the last sample in which free diazepam was still not detectable in the filtrate (cut-off 200 ng/ml = 0.7 μmol/l)

Relative albumin-binding function of binding site II (rABF II)

METHODS FOR DETERMINING AMOUNT OF FUNCTIONAL ALBUMIN

PRIORITY AND CROSS REFERENCE TO RELATED APPLICATIONS

This application is a Divisional Application of U.S. application Ser. No. 16/607,064, filed Oct. 21, 2019, now U.S. Pat. No. 11,280,780, issued Mar. 22, 2022, which is a U.S. National Phase Application under 35 U.S.C. § 371 of International Application No. PCT/EP2018/060176, filed Apr. 20, 2018, designating the U.S. and published as WO 2018/193087 A1 on Oct. 25, 2018, which claims the benefit of Deutsch Application No. DE 10 2017 206 786.1, filed Apr. 21, 2017. Any and all applications for which a foreign or a domestic priority is claimed is/are identified in the Application Data Sheet filed herewith and is/are hereby incorporated by reference in their entireties under 37 C.F.R. § 1.57.

FIELD

The present invention relates to methods for determining the relative binding capacity of albumin. The invention further relates to a method for determining the amount of functional albumin.

SUMMARY

The present invention relates to methods for determining the relative binding capacity of albumin by means of test strips. In particular, the invention relates to a method for determining the relative binding capacity of albumin that comprises the following steps: a) providing at least two measurement solutions of a test sample and of a reference sample, wherein the measurement solutions contain at least one albumin-binding marker M and this at least one albumin-binding marker M in at least one measurement solution of the test sample and of the reference sample exceeds the presumed available binding capacity of albumin and wherein the test sample contains a defined amount of albumin of unknown binding capacity and the reference sample contains the same defined amount of albumin having a reference binding capacity; b) incubating the measurement solutions under conditions that allow the at least one albumin-binding marker M to bind to albumin to form complexes of this marker M and albumin (M:A); c) removing the complexes (M:A) produced in step b); d) detecting the presence or amount of unbound marker M in the solutions after removal of the complex (M:A) by at least one test strip that allows determination of the unbound marker; and e) determining the relative binding capacity of albumin in the test sample based on the presence or detected amounts of unbound marker M in step d). The invention further relates to a method for determining the amount of functional albumin.

BRIEF DESCRIPTION OF THE DRAWINGS

FIG. 3A) Diazepam concentration [µmol/l] in the last sample in which free diazepam was still not detectable in the filtrate (cut-off 200 ng/ml=0.7 µmol/l). FIG. 3B) Relative albumin-binding function of binding site II (rABFII).

DETAILED DESCRIPTION

Figure 1:
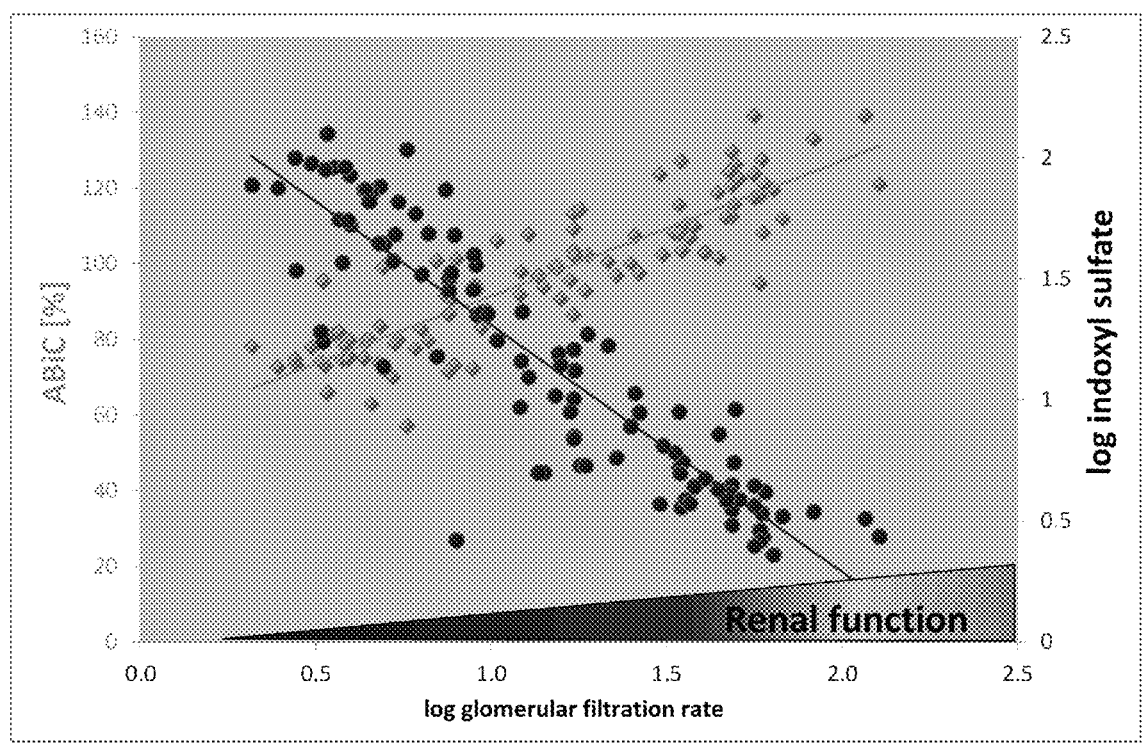
FIG. 1: Decrease in albumin function and increase in uremic toxin load with increasing severity of kidney failure
Figure 2:
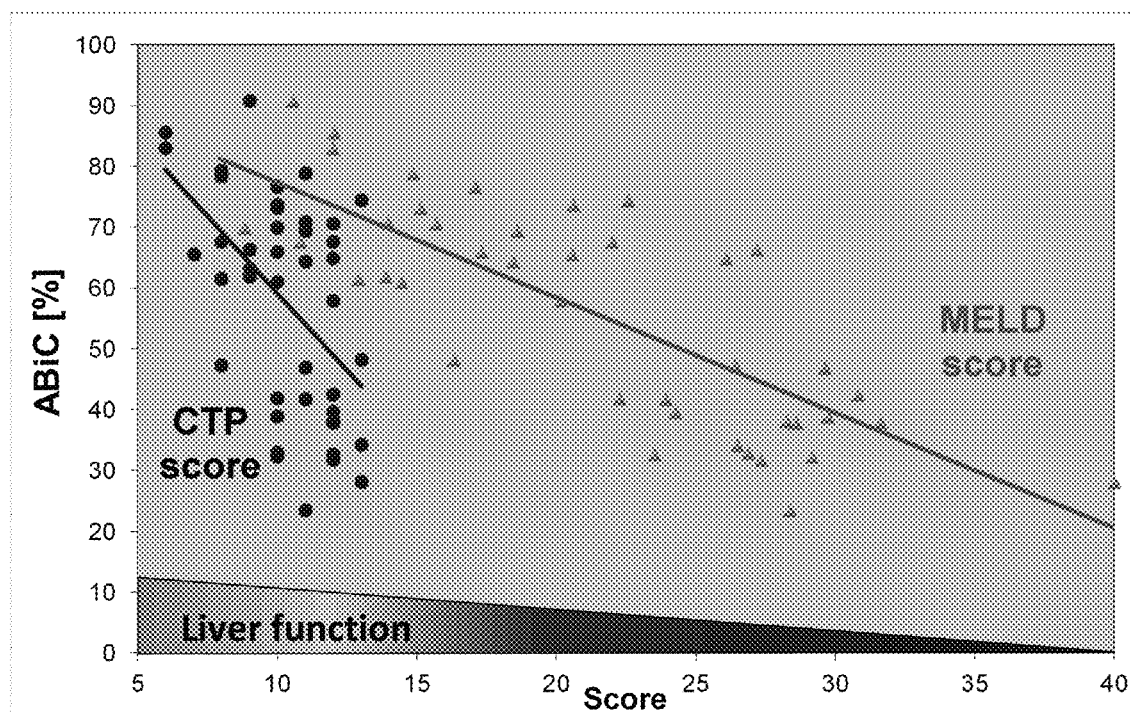
FIG. 2: Decrease in albumin function with increasing severity of liver failure, illustrated on the basis of the CHILD and MELD clinical classification systems

Albumin, which is the protein present in highest concentration in human plasma, is responsible, in addition to other functions such as the maintenance of colloid osmotic pressure, for the transport of various, mostly lipophilic substances in the body. In addition to numerous endogenous substances, metabolic products, and hormones, for example fatty acids, bilirubin, bile acids, indoxyl sulfate, tryptophane, steroids and cytokines, a large number of drugs are transported in albumin-bound form in the body (Kragh et al., Practical aspects of the ligand-binding and enzymatic properties of human serum albumin. Biol Pharm Bull 2002 June; 25(6): 695-704.)

In addition to 7 binding sites for long-chain fatty acids and a free SH group on cysteine 34, for example for nitric oxide, there are two group-specific binding sites available for the diversity of endogenous or administered (exogenous) substances. With reference to the studies on the characterization of albumin binding sites by Sudlow and coworkers, these are referred to as binding sites I and II (Sudlow G, et al., The characterization of two specific drug binding sites on human serum albumin, Mol Pharmacol 1975; 11(6): 824-832). Whereas it is mainly heterocyclic substances or dicarboxylic acids that undergo binding at binding site I, often also referred to as the warfarin/bilirubin binding site, the ligands of binding site II, often also referred to as the diazepam/indole binding site, mainly have an aromatic basic structure.

The binding of a substance to the albumin molecule can be influenced by interactions with other albumin-bound substances that are competing for the same binding site. In addition to these competitive displacement mechanisms, allosteric interactions or post-translational structural alterations of the albumin structure, for example by carbamylation or glycation, can alter the binding to albumin of exogenous toxins and endogenous substrates (Lee P., Wu X., Review: Modifications of human serum albumin and their binding effect. Curr Pharm Des 2015; 21(14): 1862-1865 and Fassano M. et al., The extraordinary ligand binding properties of human serum albumin IUBMB Life. 2005 December; 57(12): 787-96).

Under physiological conditions, the state of albumin loading is low. In individuals with impaired elimination function, for example due to liver and/or kidney failure, this can lead to an accumulation of lipophilic albumin-bound substances in the blood and thus to greater saturation of the albumin binding sites or overloading of the albumin molecule. This can result, through competitive or allosteric interactions, in an increase in the active, unbound proportion of substrates, cytokines, hormones, and drugs and can be associated with influencing metabolic feedback loops and altering pharmacological effects and also with increased side effects.

Various substances found in elevated concentrations in the plasma or cerebrospinal fluid of patients with liver failure have been identified in recent years and their significance for the clinical course of liver failure made clearer. Ammoniac, short- and medium-chain fatty acids, mercaptans, and phenols have long since been regarded as toxic substances in liver failure. Other substances such as bilirubin, bile acids or certain amino acids such as tryptophane, phenylalanine or tyrosine have been ascribed an at least indirect influence on metabolism via displacement mechanisms on the albumin molecule or as precursors for phenols or inhibitory false neurotransmitters (Sen et al., Emerging indications for albumin dialysis. Am J Gastroenterol 2005 February; 100(2): 468-475).

A number of different toxins, metabolites or cytokines are currently viewed as directly linked to complications of acute or chronic liver failure, such as hepatic encephalopathy (HE), hyperdynamic circulation, portal hypertension, cholestasis, pruritus, ascites, and hepatorenal syndrome (HRS). With increasing knowledge of the pathogenetic relationships of these substances, there is increasing focus too on the question of their therapeutic elimination and consequent influence on the severity, course or prognosis of liver failure (Hughes R D. Review of methods to remove protein-bound substances in liver failure. Int J Artif Organs 2002 October; 25(10): 911-917).

By eliminating albumin-bound substances in liver failure by means of albumin dialysis (usually in the form of the Molecular Adsorbent Recirculating System—MARS®), it was possible in randomized controlled studies to avoid or reduce complications of liver failure such as renal function, mental function (hepatic encephalopathy) or hemodynamics and to significantly reduce mortality (Heemann et al. Albumin dialysis in cirrhosis with superimposed acute liver injury: A prospective, controlled study. Hepatology 2002 October; 36(4): 949-958).

In kidney failure, inadequate elimination results in an accumulation of various uremic toxins, including low-molecular-weight albumin-bound toxins. Indoxyl sulfate and p-cresol sulfate are prototypes for these uremic toxins and are examined in clinical and experimental studies. Clinical studies have shown that the rising concentrations of albumin-bound uremic toxins associated with increasing renal insufficiency have toxic effects on the kidneys and vascular endothelium (Liabeuf et al., Protein-bound uremic toxins: new insight from clinical studies. Toxins (Basel) 2011 July; 3(7): 911-919). Indoxyl sulfate has pro-oxidative and pro-inflammatory properties and boosts expression of pro-inflammatory cytokines such as TGF-β. Moreover, toxin-dependent fibrosis of renal tissue by indoxyl sulfate was detected both in a 5/6 nephrectomy model and in a hypertensive rat model. Pro-inflammatory effects of p-cresol sulfate on leukocytes and an influence of indoxyl sulfate on aortic calcification and arterial stiffness were also demonstrated.

A direct effect of endogenous uremic toxins on the proliferation and viability of cell cultures has been confirmed. This adverse effect is likely to be functional in nature, since it was not accompanied by an increase in apoptosis (Dou et al. The uremic solutes p-cresol and indoxyl sulfate inhibit endothelial proliferation and wound repair. Kidney Int 2004 February; 65(2): 442-451). These experiments likewise showed albumin-bound uremic toxins to have an adverse effect on wound healing.

Irrespective of whether the impaired albumin function in organ failure is caused by increased loading with albumin-bound substances, allosteric interactions or by oxidative structural changes to the albumin molecule, or by a combination of these factors, it results in altered binding of endogenous substances or exogenously administered drugs and thus in an increase in the unbound fraction. However, because it is only the free fraction of a substance that is pharmacologically active, this results in a stronger effect.

A high degree of loading would be indicative of elevated free concentrations of albumin ligands and thus of greater adverse toxic effects. On the other hand, if the physiological binding function of the albumin molecule is present or restored, effects of toxins would be reduced, the physiological plasma transport of substrates and metabolites maintained, and the pharmacokinetic-pharmacodynamic relationships to be expected in drug therapy observed.

One option for determining the available binding function of the albumin molecule is to determine the individual concentration of all competing substances and their cumulative total and to estimate the degree of molar loading of the albumin molecule. However, the determination of certain ligands, for example the uremic toxins indoxyl sulfate and p-cresol sulfate, is possible only in a laborious technical process by HPLC. Even if the analysis of these two uremic toxins could be simplified to such a degree as to allow rapid analysis at the patient's bedside, the absence of any determination of the concentrations of other known, and in particular hitherto unknown, toxins would mark this approach down as unpromising.

Another approach would be to determine the albumin load regardless of the nature and fractions of the substances occupying the binding site. If such an easily determinable parameter were available, it could be used in clinical studies and its suitability as a prognostic parameter could be examined in studies with different patient populations. By analogy, for example for the determination of blood lipids and if the data situation permits this, it would then be possible to use it in routine diagnostics to assess the individual prognosis, to select the appropriate patient-specific therapy, and to monitor the therapeutic outcome and make any subsequent adjustments to the treatment plan.

Albumin function has been shown to correlate with severity of disease in both liver and kidney failure (Klammt et al. Albumin-binding function is reduced in patients with decompensated cirrhosis and correlates inversely with severity of liver disease assessed by model for end-stage liver disease. Eur J Gastroenterol Hepatol 2007 March; 19(3): 257-263.; Klammt et al. Albumin-binding capacity (ABiC) is reduced in patients with chronic kidney disease along with an accumulation of protein-bound uraemic toxins. Nephrol Dial Transplant 2011 Nov. 15; 27(6): 2377-2383). In a randomized controlled clinical trial, the elimination of albumin-bound substances was associated with an improvement in albumin function and mortality. Patients who recorded an improvement in ABiC (albumin binding capacity) in the first week of treatment showed significantly higher survival than patients with no improvement in albumin function (Klammt et al. Improvement of impaired albumin binding capacity in acute-on-chronic liver failure by albumin dialysis. Liver Transpl 2008 Aug. 28; 14(9): 1333-1339). In an initial pilot study, impaired albumin function was likewise demonstrated in the group of septic patients on the basis of the ABiC test, which correlates with severity (SAPS II) (Hinz et al., Albumin function is reduced in severe sepsis. Infection 2011; 39: S118).

EP 1 315 973 B1 discloses an indirect method for the quantitative determination of the existing binding capacity of albumin in an aqueous solution. In a preferred embodiment, the marker substance dansyl sarcosine is used and its unbound fraction determined by fluorescence spectrophotometry after binding to a defined albumin as fluorescence enhancer.

However, the fluorometric determination of the binding capacity of albumin necessitates various steps with the result that the determination in the laboratory is currently performed some time after sample collection. If simplifying the analysis could enable determination in the vicinity of the patient (point of care), this would allow individual treatment planning, for example the administration of infusions, dosage of drugs, start, duration, and intensity of extracorporeal procedures, to take account of the patient's current condition and reduce both the risk of overtreatment that is associated with side effects and underdosing that is risky for the patient.

It is therefore the object underlying the present invention to provide a rapid and simple method for determining the relative binding capacity of albumin that allows point-of-care diagnostics.

The object is achieved by the embodiments described in the claims and hereinafter.

The invention thus relates to a method for determining the relative binding capacity of albumin that comprises:
a) providing at least two measurement solutions of a test sample and of a reference sample, wherein the measurement solutions contain at least one albumin-binding marker M and this at least one albumin-binding marker M in at least one measurement solution of the test sample and of the reference sample exceeds the presumed available binding capacity of albumin and wherein the test sample contains a defined amount of albumin of unknown binding capacity and the reference sample contains the same defined amount of albumin having a reference binding capacity;
b) incubating the measurement solutions under conditions that allow the at least one albumin-binding marker M to bind to albumin to form complexes of this marker M and albumin (M:A);
c) removing the complexes (M:A) produced in step b);
d) detecting the presence or amount of unbound marker M in the solutions after removal of the complex (M:A) by at least one test strip that allows determination of the unbound marker; and
e) determining the relative binding capacity of albumin in the test sample based on the presence or detected amounts of unbound marker M in step d).

In addition to the above steps, the present method may also include further steps. A further step may, for example, be the addition of further substances, for example the addition of a substance to the test sample and reference sample to stabilize the albumin.

The method according to the present invention may preferably be automated. This allows the treatment of the test and/or reference sample(s), for example the incubation of the measurement solutions and removal of the complexes formed from this marker M and albumin (M:A) and/or detection by means of test strips and determination of the relative binding capacity of albumin, to be performed by suitable robotic instruments, analysis robots and/or be computer-assisted.

For the purposes of the present invention, "sample" is understood as meaning a solution containing albumin. It is preferably an aqueous solution having a pH of between 5 and 8, particularly preferably having a pH of between 7 and 8. The so-called "test sample" according to the invention should contain a defined amount of albumin of unknown binding capacity, whereas the so-called "reference sample" should contain the same defined amount of albumin having a reference binding capacity. What is to be understood by the term "binding capacity" is explained in detail elsewhere herein. A "defined amount" of albumin is understood as meaning an approximately defined amount of albumin that is measurable. The amount of albumin is usually determined by determining the concentration of albumin in a solution.

Methods and means for determining the albumin concentration, for example the amount of human serum albumin in the serum of a patient, are known to those skilled in the art and include, for example, determination with bromocresol green, immunochemical methods including immunoturbidimetry, and (protein) electrophoresis. It is moreover known to those skilled in the art that typically, in a human sample, between about 10 and 60 grams of albumin can be detected in one liter of blood and that human serum preferably contains about 35 to 55 grams of albumin per liter. It is additionally known to those skilled in the art that the calculated amount of albumin provides information on the number of albumin molecules present, but not on their (binding) function. A large calculated amount of albumin may, for example, exhibit low binding functionality, i.e. a marker that binds specifically to albumin may no longer bind to albumin despite the presence of albumin molecules because all the binding sites for this marker on the albumin molecules present are already occupied. Conversely, a small calculated amount of albumin may exhibit high binding functionality if, for example, certain or all of the binding sites of the albumin molecules in the solution are free. Thus, by contrast with the calculated amount of albumin, it is the functional amount of albumin, or the amount of albumin that is able to take up an albumin-binding marker M, that allows conclusions to be drawn about the binding capacity of albumin, which is explained in detail elsewhere herein.

The "test sample" according to the invention is preferably a blood, serum or plasma sample of a patient. It is further preferable if the test sample is an albumin-containing solution, i.e. an aqueous solution containing albumin, more preferably a pharmaceutical albumin preparation or cell culture supernatants.

The term "patient" generally refers to a human subject being monitored and/or treated for a medical condition, illness or similar by a healthcare professional. For the purposes of the invention, the patient is preferably a human subject with liver damage and/or renal insufficiency and/or sepsis. The patient is further preferably someone who is to receive or has received a plurality of albumin-bound drugs or substances that can bind to albumin. The terms liver damage, renal insufficiency, and sepsis include here all acute and chronic disease states. The patient preferably has chronic liver damage and/or chronic renal insufficiency and/or severe sepsis with secondary organ damage. Symptoms and characteristics of the abovementioned conditions are known to those skilled in the art and are described, for example, in standard medical textbooks such as Stedman or Pschyrembl. However, patients for the purposes of the invention may also be animals, for example mammals and in particular domestic and farm animals such as dogs, cats, horses, cows, pigs or sheep, or laboratory animals such as mice or rats.

The "reference sample" according to the invention is preferably a synthetically produced albumin solution or a sample from a healthy subject of the same species, also referred to hereinafter as a "subject". The term "synthetically produced albumin solution" covers any type of aqueous solution to which albumin has been added and/or an aqueous solution known to contain albumin. A synthetically produced albumin solution covers, for example, albumin-containing solutions such as pharmaceutical albumin preparations. For example, a synthetically produced albumin solution may be phosphate-buffered saline (PBS) to which a defined amount of albumin has been added. Albumin-containing solutions that are pharmaceutically produced and/or commercially available as medicinal products may also serve as a reference solution. According to the invention, the reference sample is particularly preferably a sample from a healthy subject, a pooled sample from several subjects, a pharmaceutical albumin-containing preparation or a synthetically produced albumin solution.

A "healthy subject" is preferably a human who is apparently healthy and is known to have no liver damage, no renal insufficiency, and no sepsis, and thus no elevated saturation of albumin binding sites or overloading of the albumin molecule. The sample from a healthy subject may, for the purposes of the invention, moreover be a "pooled" sample, i.e. a mixture from a number of healthy subjects. These are preferably pooled plasma donations from a number of healthy subjects, which may be available, for example, via blood banks. The reference sample may be largely identical to the test sample, differing only in the binding capacity of albumin, as explained in detail elsewhere herein.

The term "measurement solution" for the purposes of the present invention refers to a solution that comprises a part-volume of the test sample or of the reference sample and that contains at least one albumin-binding marker M. What is to be understood by the term "albumin-binding marker M" is explained in detail elsewhere herein. A measurement solution of the test sample may, for example, be an aliquot of the test sample or a diluted solution of the test sample to which the at least one albumin-binding marker M is added. According to the invention, at least two measurement solutions of the test sample and of the reference sample are to be provided, wherein the albumin-binding marker M exceeds the presumed available binding capacity of albumin (as explained elsewhere herein) in at least one measurement solution of the test sample and of the reference sample. The measurement solution should preferably have a pH of between 5 and 8, particularly preferably between 7 and 8. The measurement solution may also contain additional substances, for example buffers and/or stabilizers used to stabilize the pH and/or to stabilize the albumin. It is known to those skilled in the art that the albumin concentration in the serum of a healthy subject is about 35 to 55 grams per liter, which means that a part-volume, for example a diluted solution of the serum, should have an albumin concentration of less than 55 grams per liter. It is also known to those skilled in the art that different measurement solutions having varying molar ratios of marker M and albumin may be produced through dilution series of the test sample and of the reference sample, on adding constant amounts of marker M, or by dividing the test sample and the reference sample into aliquots and adding varying amounts of marker M. Preference is given to molar ratios (marker M/albumin) of, for example, 1, 0.5, 0.3, 0.25, 0.2, 0.15, 0.1, and 0.05. According to the invention, the marker M should exceed the presumed available binding capacity of albumin in at least one measurement solution of the test sample and of the reference sample, as explained elsewhere herein.

According to the invention, at least two measurement solutions of the test sample and of the reference sample need to be provided. The provision of at least two measurement solutions means that preferably two measurement solutions of the test sample and two measurement solutions of the reference sample are provided. Step a) of the method according to the invention thus comprises preferably the provision of at least two measurement solutions each of a test sample and of a reference sample. It is further preferable to provide at least 3, 4, 5, 6, 7 or 8 measurement solutions of the test sample and of the reference sample. For example, the test sample and the reference sample may each be split into 6 aliquots that contain the same defined amount of albumin. This is followed by addition of different amounts of an albumin-binding marker M to give decreasing molar ratios of marker to albumin in the respective aliquots of the test sample and of the reference sample. Alternatively, increasing dilutions of the test sample and of the reference sample may be prepared, for example 6 dilutions of the test sample and of the reference sample, each containing different amounts of albumin, may be prepared. This is followed by the addition of equal amounts of an albumin-binding marker M so that varying molar ratios of marker to albumin are in turn present in the respective 6 dilutions of the test sample and of the reference sample. According to the invention, in at least one measurement solution of the test sample and of the reference sample here, the at least one albumin-binding marker M needs to exceed the presumed available binding capacity of albumin, i.e. so that the marker is present in "excess" relative to the binding capacity of albumin. Incubation of the at least 2, preferably also 3, 4, 5, 6, 7 or 8 measurement solutions results in the albumin-binding marker M being able to bind to at least one defined albumin binding site and the formation of complexes from the marker and albumin (M:A). After removal of the complexes (M:A) formed, the amount of unbound marker M may be detected through the use of at least one test strip. This detection must be possible in at least one of the measurement solutions of the test sample and of the reference sample. It is accordingly then possible, for example, to determine which of the at least 2, preferably 3, 4, 5, 6, 7 or 8 measurement solutions of the reference sample is the measurement solution in which unbound marker M is first detectable using at least one test strip and to determine which of the at least 2, preferably 3, 4, 5, 6, 7 or 8 measurement solutions of the test sample is the measurement solution in which no unbound marker M is last detectable using at least one test strip. What exactly is to be understood by the term "test strip" is explained in detail elsewhere herein. Based on the detected amounts of unbound marker M, it is then possible to determine the relative binding capacity of albumin, also referred to as the relative binding function of albumin, which provides information on the binding site-specific loading state and on the remaining available binding capacity of albumin at the defined binding site(s), as also explained in more detail elsewhere herein.

For the purposes of the invention, the term "binding capacity of albumin" is understood as meaning the capacity of the albumin to take up/bind one or more substances that bind specifically to albumin. The term binding capacity covers the uptake capacity of one or more substances at one and/or more binding sites. When the binding capacity at a particular binding site, for example binding site I and/or II, is reached, this may also be referred to as "binding site I and/or II saturation". For example, if a substance such as diazepam, which binds specifically to binding site II, completely blocks binding site II, binding site II is saturated and excess diazepam still present in the solution is no longer able to bind to albumin. The formation of complexes of albumin and diazepam in said solution (with albumin saturated at binding site II) is accordingly no longer possible and any diazepam present remains unbound in the solution. The binding capacity of albumin is therefore to be regarded as a functional property of albumin. As previously mentioned above, a large amount or high concentration of albumin may, for example, exhibit low binding functionality ("bad albumin" for an albumin-binding marker), whereas a small amount or low concentration of albumin may exhibit high binding functionality ("good albumin" for an albumin-binding marker).

The term "reference binding capacity" refers to an assumed or known binding capacity. This may, for example, be the binding capacity of a synthetic solution to which albumin has been added and of which it is known that the binding sites of the albumin are unoccupied. It can additionally be a sample, preferably a serum or plasma sample, from a healthy subject, preferably a subject without liver damage or renal insufficiency, in whom pronounced saturation of the albumin binding sites or overload of the albumin molecule are known to be absent. Thus, in comparison to an unwell patient, preferably a patient with liver damage and/or renal insufficiency, the binding capacity of albumin in the sample from the healthy subject (i.e. the reference sample) will be known or assumed to be higher than would be the case in said patient (i.e. in the test sample).

The "relative binding capacity of albumin", also referred to as the "relative binding function of albumin", which is determined by the method according to the invention, provides information on the binding site-specific loading state and on the remaining available binding capacity of albumin at said binding site(s). According to the invention, a substance that can bind to albumin is also referred to as an albumin ligand or albumin-binding marker, as described elsewhere herein.

The term "exceeding the binding capacity" of albumin means that an albumin-binding marker M is no longer able to bind to albumin and thus exceeds the binding capacity of albumin. For example, if more marker M is added to a solution containing albumin than is able to bind specifically to the albumin present in the solution, the marker exceeds the binding capacity of albumin. Unbound marker M that is not bound to albumin/is not present in marker:albumin (M:A) complexes will then be detectable in the solution (preferably after removal of marker:albumin complexes). For example, if binding site II is completely occupied by a specific marker such as diazepam, i.e. binding site II is saturated, the addition or presence of diazepam that is now no longer able to bind to albumin (because the binding site is saturated) results in the binding capacity at said binding site II being exceeded. However, in a solution containing albumin in which binding site II is already saturated, any further markers that, for example, bind specifically to binding site I may continue to be taken up by the albumin present in the solution until binding site I is likewise saturated. The presumed available binding capacity or an exceeding of this binding capacity is thus dependent on the pre-existing loading state of the albumin molecule and the availability of binding site(s) to which the albumin-binding marker(s) bind. Moreover, it is known to those skilled in the art that, even if the binding capacity of the individual binding sites is altered by allosteric interactions or by structural changes in the albumin molecule, account will likewise be taken of these changes in binding properties. As already mentioned above, it can be assumed that the presumed available binding capacity of albumin in a sample from a patient with liver damage and/or renal insufficiency will be lower than in a sample from a healthy subject, since liver damage and/or renal insufficiency are known to be able to result in increased saturation or albumin overloading.

What is more, exceeding the binding capacity of albumin for an albumin-binding marker M should according to the invention result in the presence of "excess"/unbound marker M in the sample, i.e. unbound marker M in at least one measurement solution of the test sample and of the reference sample, being detectable after removal of the marker:albumin complexes (as described in detail elsewhere herein). It is preferable if the excess/unbound marker M, particularly preferably the unbound marker diazepam, is present in a concentration of at least 100 ng/ml, at least 200 ng/ml, at least 300 ng/ml, at least 400 ng/ml or at least 500 ng/ml.

The term "albumin-binding marker M" is according to the invention understood as meaning a substance that can bind specifically to albumin. It is possible here for the albumin-binding marker M to bind to one or more binding sites in the albumin. According to the invention, the albumin-binding marker M binds preferentially to binding site I and/or II of albumin. This includes, for example, substances known to those skilled in the art that have been shown to be able to bind to the respective binding sites of albumin, for example diazepam, other benzodiazepines, tryptophane, bile acids, dansyl sarcosine, medium-chain fatty acids, warfarin, furosemide, sulfonylureas, and dansyl amide, or even opioids such as fentanyl, synthetic drugs such as cocaine, or cannabinoids.

For the purposes of the invention, the albumin-binding marker M is preferably a benzodiazepine, particularly preferably diazepam. The method according to the invention is to include at least one albumin-binding marker M. The use of multiple markers is, however, also preferred, for example it is possible to use a combination of markers that bind to different binding sites in the albumin molecule or a combination of markers that bind to the same binding site, for example to binding site I of albumin. Markers that bind to the same binding site may in turn be substances that bind with equal, similar or different binding strength to defined binding site(s), for example binding site I of albumin.

The term "binding site I"/"binding site II" of albumin refers to two binding sites of albumin to which substances can specifically bind. It is known to those skilled in the art that, in addition to 7 binding sites for long-chain fatty acids and a free SH group on cysteine 34, for nitric oxide for example, albumin has two group-specific binding sites available for the diversity of endogenous or administered (exogenous) substances. With reference to the studies on the characterization of the albumin binding sites by Sudlow and co-workers, these are referred to as binding sites I and II (Sudlow G, et al., The characterization of two specific drug binding sites on human serum albumin Mol Pharmacol 1975; 11(6): 824-832). Those skilled in the art will moreover be aware that binding site I of albumin is often referred to as the warfarin/bilirubin binding site and binds mainly heterocyclic substances or dicarboxylic acids, whereas binding site II is often also referred to as the diazepam/indole binding site and binds mainly ligands having an aromatic basic structure. For example, warfarin, furosemide or dansyl amide bind preferentially to binding site I, whereas indoles such as tryptophane or else diazepam, bile acids, dansyl sarcosine and medium-chain fatty acids bind preferentially to binding site II (Peters T. All about albumin: biochemistry, genetics, and medical applications. Academic Press, 1996; Ghuman J et al., Structural basis of the drug-binding specificity of human serum albumin. J Mol Biol (2005); 353: 38-52).

According to the invention, the incubation of the measurement solutions is to be carried out under conditions that allow the at least one albumin-binding marker M to bind to albumin to form complexes of this marker M and albumin (M:A). These are preferably complexes of a benzodiazepine, preferably diazepam, and albumin. The incubation of the measurement solutions should preferably take place at room temperature for up to 30 minutes, particularly preferably for at least 10 seconds, 20 seconds, 45 seconds, 1 minute, 2 minutes, 5 minutes, 10 minutes, 15 minutes, 20 minutes or 30 minutes.

The term "removal of the complexes" is understood as meaning the separation of the complexes formed from at least one albumin-binding marker M and albumin (M:A complexes) from the measurement solution. Methods and means of removing M:A complexes, preferably diazepam-albumin complexes, are known to those skilled in the art and include, for example, centrifugation, filtration or specific adsorption methods such as immunoadsorption. Removal of the M:A complexes leaves a solution, for example an albumin-free filtrate, in which M:A complexes are no longer present. The presence and/or amount of unbound marker M can now be determined in this solution, respectively.

The term "detection" as used herein includes the qualitative, semiquantitative, and/or quantitative determination of the presence of unbound marker M in a solution. The term "detecting the presence or amount of unbound marker M" is understood as meaning the detection of unbound marker M in at least one measurement solution of the test sample or of the reference sample after removal of the M:A complexes (as explained above). The term amount should be understood here not in the sense of an absolute amount, but rather as a semiquantitative statement, for example in the sense of a minimum amount above which the presence of the unbound marker is possible based on the detection limit of the test strip used. Detecting the presence or amount of unbound marker M consists preferably of determining the qualitative presence of unbound marker, i.e. a yes or no statement as to whether unbound marker is present in the solution into which the test strip is dipped.

The term "detection limit", also referred to as the limit of detection, is understood as meaning the extreme value of a measurement method down to which the measured variable can still be reliably detected. For example, if a test strip for diazepam with a predetermined detection limit of 100 ng/ml is used, a corresponding "positive" signal for the test strip means it is possible to conclude that unbound marker is present in said solution in a content of at least 100 ng/ml or, if a corresponding "negative" signal is obtained for the test strip, it can be concluded that unbound marker is absent or is present in an amount that is too small to be detected. It is known to those skilled in the art that the corresponding signals, which are to be regarded as either positive or negative, depend on the substance to be detected and/or test strip used and/or derive from the detection method of the test strip. The predetermined detection limit is according to the invention preferably at least 1 ng/ml, 10 ng/ml, 50 ng/ml, 100 ng/ml, 200 ng/ml, 300 ng/ml, 400 ng/ml or 500 ng/ml.

The term "tolerance limit", also referred to as "cut-off", is understood as meaning the value or limit below/above which below/above which a test result is to be evaluated as positive or negative. To ensure reliability of detection in a test or test strip and thus to avoid "false positive" results, the tolerance limit (cut-off) is usually several times higher than the detection limit. The tolerance limit may, however, also be the same as the detection limit. In a strip test, a so-called "positive signal" is usually obtained when the marker concentration, for example the amount of unbound diazepam in the solution after removal of the M:A complexes, is below the specified tolerance limit (for example a cut-off value of 200 ng/ml). Preferred tolerance limits for test strips according to the invention, preferably for a benzodiazepine, particularly preferably for diazepam, are about 100 ng/ml, 200 ng/ml, 300 ng/ml, 400 ng/ml, 500 ng/ml, and 600 ng/ml.

It is also known to those skilled in the art that there are varying preferred tolerance limits for individual substances or test strips. For example, the tolerance limits may depend on the substance to be detected and/or the test strip used and/or the detection method of the test strip. In addition, there may also be pertinent regulatory aspects, for example guidelines and requirements of the US National Institute on Drug Abuse (NIDA) for the approval of test strips for the detection of drugs such as cocaine or amphetamine. This is to ensure that the decision, i.e. the threshold above which a test result is to be evaluated as positive or negative, meets specific requirements. For example, a test strip for opiates needs to ensure that the consumption merely of a poppyseed bun does not give a positive signal and that the presence of opiates is judged to be positive only above a certain amount. For standard drug tests and corresponding test strips that are approved by the NIDA, the tolerance limit is often much higher, e.g. hundreds or thousands of times higher, than the detection limit of the substance to be detected. Test strips with different tolerance limits (cut-offs) for different substances are known to those skilled in the art. For example, tolerance limits are preferably about 300 ng/ml, 500 ng/ml, 1000 ng/ml or 3000 ng/ml for the detection of amphetamine, about 100 ng/ml, 150 ng/ml, 300 ng/ml or 400 ng/ml for cocaine, about 20 ng/ml or 100 ng/ml for fentanyl, about 300 ng/ml, 1000 ng/ml or 2000 ng/ml for opiates such as morphine, about 20 ng/ml, 50 ng/ml, 150 ng/ml or 500 ng/ml for marijuana (THC), about 100 ng/ml or 200 ng/ml for oxycodone, about 25 ng/ml or 50 ng/ml for phencyclidine, and about 300 ng/ml, 500 ng/ml or 1000 ng/ml for methamphetamine.

The term "test strip" covers any test strips or strip tests that can be used to detect a specific marker, preferably an albumin-binding marker M. Preference is given to test strips for use in aqueous solutions, preferably having a pH of between 5 and 8, particularly preferably having a pH of between 7 and 8. Test strips for detecting benzodiazepines are known to those skilled in the art. In addition, it is known to those skilled in the art that—depending on the test strip used—the presence or absence of a signal may mean a positive result. For example, commercially available test strips for benzodiazepines often employ a competitive immunoassay. Detection in this case does not use a second, labeled antibody, but a labeled competitor antigen (a synthetic compound that is structurally similar to the analyte, for example diazepam, and also binds to the antibody). This means there is competition between analyte (diazepam) and competitor for a binding site on the antibody. The signal here behaves inversely to the analyte concentration, i.e. little analyte=almost all antibody binding sites are occupied by labeled competitor⇒intense color reaction; much analyte⇒weak color reaction. For the purposes of the invention, it is preferably a test strip that is based on an immunochemical test for rapid detection of an albumin-binding marker having a visually readable result. For example, a test strip based on a competitive sandwich ELISA that allows the detection of benzodiazepines with a cut-off of 300 ng/ml by means of a visually readable control line and test line. If a benzodiazepine is present in the solution here, a colored line appears (control line). If no benzodiazepine is present in the solution, two colored lines appear (test and control line).

According to the invention, the at least one test strip is intended to allow the determination of unbound marker M in the solutions after removal of the complexes of the marker and albumin (M:A) as described elsewhere herein. Preference is moreover given to the use of more than one test strip, preferably 3, 4, 5 or 6 test strips, having different predetermined detection limits and/or different predetermined tolerance limits for one or more albumin-binding marker(s) M.

As already mentioned above, in most test strips a so-called "positive signal" is obtained when the marker concentration, for example the amount of unbound diazepam in the solution after removal of the M:A complexes, is below the specified tolerance limit, for example a cut-off value of 200 ng/ml. For example, if two test strips are then used in said solution, with the first test strip having a cut-off of 200 ng/ml and the second a cut-off of 300 ng/ml, this allows direct, semiquantitative estimation of the free diazepam concentration in the solution. In this example, the free diazepam concentration is accordingly less than 200 ng/ml if a signal is generated in both test strips used; if neither test strip gives a detectable test signal, the diazepam concentration in the solution is above 300 ng/ml. However, if a signal is observed on the test strip with a 300 ng/ml cut-off, but not on the test strip with the 200 ng/ml cut-off, the diazepam concentration in the solution can be reported as being in the range between 200 and 300 ng/ml. Thus, through suitable selection and combinations of test strips, semiquantitative estimation of the diazepam concentration in said solution is possible, thereby allowing determination of the relative albumin-binding function.

According to the invention, preference is given to the use of test strips that allow the detection of benzodiazepines, particularly preferably diazepam, or of synthetic drugs such as amphetamines, cannabis, methadone or opiates. Further preference is given to test strips having different predetermined detection limits and/or different predetermined tolerance limits for one or more albumin-binding marker(s) M that are combined on a common carrier.

The "relative binding capacity of albumin" can also be referred to as the relative albumin-binding function (rABFx) or "ABiC" (albumin binding capacity). The determination of the relative binding capacity of albumin is based, according to the invention, on the amounts of unbound marker in the solutions detected by means of test strips after removal of the marker:albumin (M:A) complexes.

The relative binding capacity of albumin (rABFx) is preferably determined according to the following formula:

$$rABFx = \frac{mD_S}{mD_R}$$

where x serves as the identifier of the specific binding site (for example binding site I or II) and mDR and mDS represent the measurement solution/molar dilution or ratio of marker to albumin (mD) at which respectively, by means of test strips according to the invention, unbound marker is first detected in the reference (mDR) and no unbound marker is last detected in the sample (mDS). If the molar dilution/measurement solution at which unbound marker is first detected in the filtrate is lower in the sample than in the reference, the relative binding capacity of albumin is less than 1. If the two molar dilutions are equal, the relative binding capacity of albumin is 1.

Compared to the known methods of the prior art, the method according to the invention is fast, efficient, inexpensive, and can be used without any special infrastructure requirements. The method according to the invention makes determination of determination of the relative binding capacity of albumin in the vicinity of the patient, i.e. point-of-care diagnostics, possible. This means that account can be taken of the patient's current condition when planning treatment, for example the administration of infusions, dosage of drugs, and start, duration, and intensity of extracorporeal procedures may be adjusted accordingly, thereby reducing side effects of overtreatment or the risk of underdosing the patient.

The definitions and explanations of terms provided previously likewise apply to the embodiments described hereinafter.

In a preferred embodiment of the method according to the invention, the at least one albumin-binding marker M binds to binding site I and/or II of albumin.

In another preferred embodiment of the method according to the invention, the at least one albumin-binding marker M is a benzodiazepine. It is particularly preferable if the at least one albumin-binding marker M is diazepam.

In a further preferred embodiment of the method according to the invention, the at least one test strip has a predetermined detection limit and/or a predetermined tolerance limit for the at least one albumin-binding marker M.

In a further preferred embodiment of the method according to the invention, a plurality of test strips is used for different albumin-binding markers M.

In a further preferred embodiment of the method according to the invention, the defined detection limit for the albumin-binding marker M is at least 100 ng/ml and/or a predetermined tolerance limit is about 200 ng/ml.

In a further preferred embodiment of the method according to the invention, the test sample is a sample from a patient with liver damage and/or renal insufficiency and/or sepsis or an albumin-containing solution.

In a further preferred embodiment of the method according to the invention, the reference sample is a sample from a healthy subject or a synthetically produced albumin solution.

The invention further relates to a method for determining the amount of functional albumin, comprising:
 a) providing a test sample containing a defined amount of albumin of unknown binding capacity and a reference sample containing the same defined amount of albumin having a reference binding capacity;
 b) incubating the test sample and reference sample with a defined amount of at least one albumin-binding marker M to the test sample and to the reference sample under conditions that allow the at least one albumin-binding marker M to bind to albumin to form complexes of this marker M and albumin (M:A);
 c) removing the complexes (M:A) formed in step c);
 d) detecting the amount of unbound marker M in the samples after removal of the complex (M:A) through a first and a second test strip that allow determination of the amount of unbound marker, with the test strips having different predetermined tolerance limits; and
 e) determining the amount of functional albumin based on the detected amounts of marker M in step d).

The test sample and the reference sample are for the purposes of the invention a solution containing albumin, as explained in detail elsewhere herein. This is, moreover, an in vitro method. The provision of a sample does not according to the invention comprise a method that is carried out on the human body.

In a preferred embodiment of the method according to the invention, the first test strip has a predetermined tolerance limit, particularly preferably for diazepam, of about 200 ng/ml and/or the second test strip has a predetermined tolerance limit of about 300 ng/ml.

It is further preferable if a tolerance limit for the detection of an amphetamine is about 300 ng/ml for the first test strip and about 500 ng/ml for the second test strip, a tolerance limit for the detection of cocaine is about 100 ng/ml for the first test strip and about 300 ng/ml for the second test strip, a tolerance limit for the detection of fentanyl is about 20 ng/ml for the first test strip and about 100 ng/ml for the second test strip, a tolerance limit for the detection of an opiate such as morphine is about 300 ng/ml for the first test strip and about 1000 ng/ml for the second test strip, a tolerance limit for the detection of marijuana (THC) is about 20 ng/ml for the first test strip and about 150 ng/ml for the second test strip, a tolerance limit for the detection of oxycodone is about 100 ng/ml for the first test strip and about 200 ng/ml for the second test strip, a tolerance limit for the detection of phencyclidine is about 25 ng/ml for the first test strip and about 50 ng/ml for the second test strip, a tolerance limit for the detection of methamphetamine is about 300 ng/ml for the first test strip and about 500 ng/ml for the second test strip.

Preference is moreover given to the use of more than one test strip, preferably 3, 4, 5 or 6 test strips having different predetermined detection limits and/or different predetermined tolerance limits for one or more albumin-binding marker(s) M. According to the invention, preference is given to the use of test strips that allow the detection of benzodiazepines, particularly preferably diazepam, or of synthetic drugs such as amphetamines, cannabis, methadone or opiates. Further preference is given to test strips having different predetermined detection limits and/or different predetermined tolerance limits for one or more albumin-binding marker(s) that are combined on a common carrier.

According to the invention, the amount of unbound marker M in the samples after removal of the complex (M:A) is determined by means of at least two test strips having different tolerance limits. Further preference is given to the use of more than two test strips, preferably 3, 4, 5, 6, 7 or 8 test strips having different tolerance limits and/or combinations of a plurality of strip tests having different tolerance limits (cut-off values).

For example, by using a plurality of test strips specific for marker M (preferably diazepam) having different cut-off values such as 100 ng/ml, 200 ng/ml, 300 ng/ml, 400 ng/ml, and 500 ng/ml that are combined on a carrier, it is possible to determine the amount of unbound marker M in a sample and for a reference solution (both of approximately the same albumin concentration and containing approximately the same amount of albumin-binding marker M) and to deduce from this the functional albumin fraction and the albumin-binding function.

The determination of the relative binding capacity and the calculation of the relative albumin-binding function (rABFx) can preferably be determined according to the following formula:

$$rABFx = \frac{C_R}{C_S}$$

where x serves as the identifier of the specific binding site (for example I or II) and CS or CR as the amount/concentration of the unbound marker in the sample (CS) and reference (CR) after step d) of the method according to the invention, for example the diazepam concentration in the filtrate after removal of the marker albumin:marker (M:A) complexes in the test sample and reference sample according to the invention.

In a further preferred embodiment of the method according to the invention, the at least one albumin-binding marker M binds to binding site I and/or II of albumin.

In another preferred embodiment of the method according to the invention, the at least one albumin-binding marker M is a benzodiazepine. It is particularly preferable if the at least one albumin-binding marker M is diazepam.

In a further preferred embodiment of the method according to the invention, the test sample is a sample from a patient with liver damage and/or renal insufficiency and/or sepsis or an albumin-containing solution.

In a further preferred embodiment of the method according to the invention, the reference sample is a sample from a healthy subject or a synthetically produced albumin solution.

The invention further covers a method in which the detection of the presence/amount of unbound marker M may be performed directly in the test sample and the reference sample without having to perform a separation step and/or removal of albumin:marker (M:A) complexes, respectively. This is achieved by using at least one test strip that reacts specifically with the unbound marker M. For example, the test strip(s) may be encased in a synthetic or biological membrane having a defined pore size that allows only the unbound marker molecules to come into direct contact with the test strip, whereas the albumin-bound marker molecules are held back because of the size of the albumin molecule and thus cannot be detected.

The content of all references cited herein is hereby incorporated by reference to the content of the relevant specific disclosures and in its entirety.

EXAMPLES

The following examples are provided as illustration of the invention. They should not be construed in a restrictive manner with regard to the scope of protection.

Example 1: Principle of Determining the Relative Albumin Function (rABF) or Relative Binding Capacity of Albumin To an albumin-containing sample S is added a specific marker M that binds to the albumin molecule and the amount of unbound marker MS is quantified by means of a strip test. In parallel, the same amount of the specific marker M is added to an albumin-containing reference solution R having the same albumin concentration as the sample S and the amount of unbound marker MR in the reference solution is likewise detected.

Example 2: Detecting the Presence of Unbound Markers by Means of a Marker-Specific Strip Test To multiple aliquots of a sample P and of a reference R, all having the same albumin concentration, are added different amounts of marker so as to obtain a series of descending marker/albumin molar ratios for the sample and for the reference (for example 0.3, 0.25, 0.2, 0.15, 0.1, and 0.05). Following a separation step, the presence of the unbound marker in the albumin-free filtrates of the individual molar ratios for the sample and for the reference is analyzed by means of a marker-specific test strip having a defined cut-off (for example 200 ng/ml for diazepam). The relative albumin-binding function (rABF) is determined according to the following formula:

$$rABFx = \frac{mD_S}{mD_R}$$

where x serves as the identifier of the specific binding site (for example I or II) and mDR and mDS are the molar dilutions at which respectively, in the filtrate by means of the strip test, unbound marker is first detected in the reference and no unbound marker is last detected in the sample.

If the molar concentration at which unbound marker is first detected in the filtrate is lower in the sample than in the reference, the relative albumin-binding function has a value of less than 1. If the two molar dilutions are equal, the relative albumin-binding function is 1.

Example 3: Method for Determining the Amount of Functional Albumin/Detecting the Unbound Amount of Marker by Means of Combinations of Strip Tests with Different Cut-Off Values To a sample S and to a reference R, both having the same albumin concentration, is added the amount of marker M and, after a separation step, the concentration of the unbound marker in the albumin-free filtrate of the reference and of the sample is determined using marker-specific test strips with different cut-off values (for example 100, 200, 300, 400, 500 ng/ml for diazepam) and the relative albumin-binding function (rABF) is determined according to the following formula:

$$rABFx = \frac{C_R}{C_S}$$

where x serves as the identifier of the specific binding site (for example I or II) and $C_R$ and $C_S$ as the diazepam concentration in the filtrate of the sample and reference respectively.

Detection of the amount of unbound marker by means of a marker-specific strip test could also take place in the sample P and in the reference (without a separation step), provided it can be ensured that only the amount of unbound marker can be detected by the strip test. This could, for example, be achieved by encasing the test strip(s) in a membrane (synthetic or biological) having a defined pore size that allows only the unbound marker molecules to come into direct contact with the test strip, while the albumin-bound marker molecules are held back because of the size of the albumin molecule and cannot be detected.

Example 4: Determining the Relative Binding Capacity of Albumin in Plasma Samples from Patients with Chronic Liver Damage and Patients with End-Stage Renal Insufficiency A plasma sample is divided into aliquots and PBS is added so as to obtain 8 aliquots with a volume of 0.9 ml and an albumin concentration of 83.3 µmol/l. To each of these aliquots is added 0.1 ml of diazepam solutions of different diazepam concentration so as to obtain 6 aliquots with an albumin concentration of 75 µmol/l and diazepam concentrations of 18, 15, 12, 9, 6, and 3 µmol/l (corresponding to a molar ratio of diazepam to albumin of 0.24, 0.2, 0.16, 0.12, 0.08, and 0.04).

After an incubation period, the unbound amounts of marker are separated by centrifugation (Centrisart Sartorius, cut-off 20000 daltons). The amount of diazepam in the filtrate is then determined by means of a strip test (test strip cut-off 200 ng/ml). In the strip test used, a signal is obtained if the diazepam concentration in the liquid (filtrate) is below the specified cut-off value (200 ng/ml). The sample (or diazepam concentration) is determined at which the signal is last detectable, i.e. the last concentration in the filtrate that was below the cut-off value. The same is done using a reference sample (e.g. healthy control) and the diazepam concentration at which the signal of the test strip was last observed in the ultrafiltrate is determined here too. The ratio of these two concentrations is calculated and the relative albumin-binding function of binding site II (rABF II) is determined according to the formula below.

$$rABF\ II = \frac{M_R}{M_S} \text{ or } \frac{C_{MS}}{C_{MR}}$$

where $M_R$ and $M_S$ are the amount of unbound marker (if determining the concentrations) or $C_{MS}$ and $C_{MR}$ are the concentration/dilution of the added marker at which respectively, in the filtrate by means of the strip test, unbound marker is first detected in the reference and NO unbound marker is last detected in the sample.

Figure 3A:
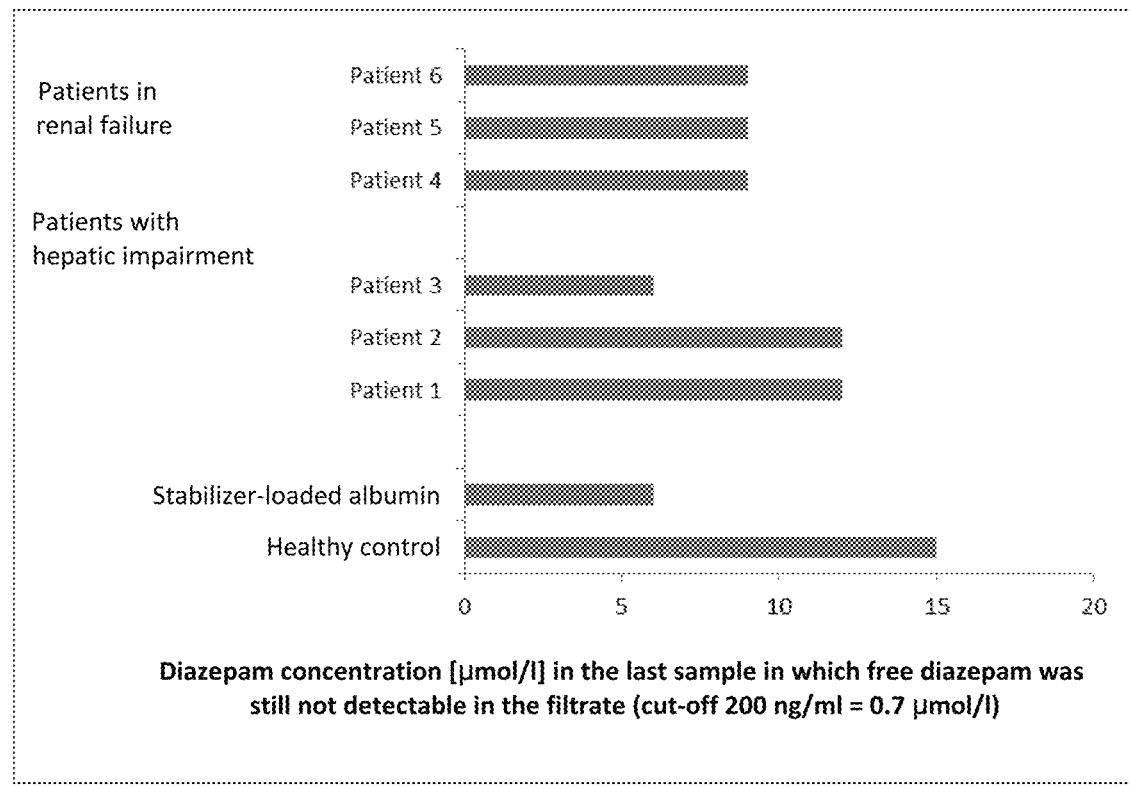
FIGS. 3A and 3B: Determination of the relative binding capacity of albumin in plasma samples from patients with chronic liver damage (patients 4, 5, 6) and patients with end-stage renal insufficiency (patients 1, 2, 3), in a stabilizer-containing pharmaceutical albumin preparation, and in plasma from a healthy volunteer.
Figure 3B:
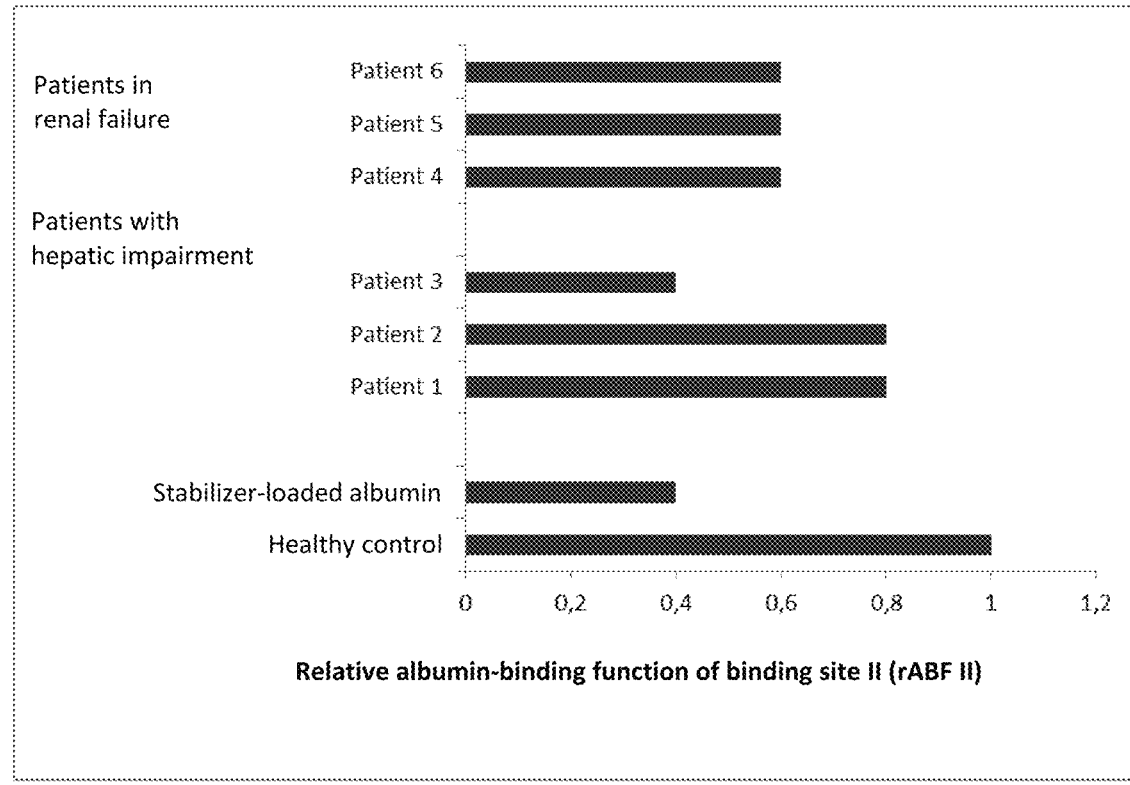

This was done using plasma from a healthy volunteer (reference), a stabilizer-containing pharmaceutical albumin preparation, and 3 plasma samples from patients with chronic liver damage and 3 patients with end-stage renal insufficiency (see FIGS. 3A/3B).

Example 5: Semiquantitative Estimation of the Diazepam Concentration by Means of Test Strips Having Different Detection Limits A plasma sample is diluted with PBS so that the albumin concentration in the sample is then 677 µmol/l. To 1.8 ml of this sample is added 0.2 ml of a diazepam solution having a concentration of 500 µmol/l so that the sample then has an albumin concentration of 600 µmol/l and a diazepam concentration of 50 µmol/l, which corresponds to a diazepam/albumin molar ratio of 0.083.

After an incubation period, the unbound amounts of marker are separated by centrifugation (Centrisart Sartorius, cut-off 20000 daltons). The diazepam concentration in the filtrate is then determined by means of (at least) two different strip tests (test strip cut-off 200 ng/ml and 300 ng/ml). In the strip test used, a signal is obtained if the diazepam concentration in the liquid (filtrate) is below the specified cut-off value (200 or 300 ng/ml). Estimation of the free diazepam concentration in the filtrate is thus possible. In our working example, the free diazepam concentration accordingly is less than 200 ng/ml if a signal is generated in both test strips used; if neither test strip gives a detectable test signal, the diazepam concentration in the filtrate is above 300 ng/ml.

However, if a signal is observed on the test strip with a 300 ng/ml cut-off, but not on the test strip with the 200 ng/ml cut-off, the diazepam concentration in the filtrate can be reported as being in the range between 200 and 300 ng/ml.

Thus, through suitable selection and combinations of test strips, semiquantitative estimation of the diazepam concentration in the filtrate is possible, thereby allowing determination of the relative albumin-binding function.

What is claimed is:
1. A method for determining an amount of functional albumin, the method comprising:

a) providing a test sample containing a defined amount of albumin of unknown binding capacity and a reference sample containing the same defined amount of albumin having a reference binding capacity;
b) incubating the test sample and reference sample with a defined amount of at least one albumin-binding marker M under conditions that allow the at least one albumin-binding marker M to bind to albumin (A) to form complexes of the at least one albumin-binding marker M and albumin (M:A);
c) removing the complexes (M:A) formed in step c);
d) detecting a presence or an amount of unbound marker M in the samples after removal of the complexes (M:A) through first and second test strips that allow for a determination of an amount of unbound marker M, wherein the first and the second test strips have different detection limits/tolerance limits for the marker M, wherein said detecting is qualitative or semiquantitative detecting in which the unbound marker is detected based on the detection limit of the test strip; and
e) determining the amount of functional albumin based on the presence or the amounts detected of marker M in each of the first and second test strips in step d).

2. The method of claim 1, wherein the at least one albumin-binding marker M binds to binding site I and/or II of albumin.

3. The method of claim 1, wherein the at least one albumin-binding marker M is a benzodiazepine.

4. The method of claim 3, wherein the benzodiazepine is diazepam.

5. The method of claim 1, wherein the first and the second test strips has a predetermined detection limit and/or a predetermined tolerance limit for the at least one albumin-binding marker M.

6. The method as claimed in claim 5, wherein the predetermined detection limit for the albumin-binding marker M is at least 100 ng/ml.

7. The method as claimed in claim 5, wherein the predetermined tolerance limit is about 200 ng/ml.

8. The method of claim 5, wherein the first test strip has a predetermined tolerance limit of about 200 ng/ml.

9. The method of claim 5, wherein the second test strip has a predetermined tolerance limit of about 300 ng/ml.

10. The method of claim 1, wherein a plurality of test strips is used for different albumin-binding markers M.

11. The method of claim 1, wherein the test sample is a sample from a patient with liver damage and/or renal insufficiency and/or sepsis.

12. The method of claim 1, wherein the test sample is an albumin-containing solution.

13. The method of claim 1, wherein the reference sample is a sample from a healthy subject or a synthetically produced albumin solution.

* * * * *